United States Patent [19]

Papajohn

[11] 4,421,512
[45] Dec. 20, 1983

[54] PANTYHOSE WITH SANITARY NAPKIN HOLDER

[76] Inventor: Elissa D. Papajohn, 65 Montague St., Brooklyn, N.Y. 11201

[21] Appl. No.: 323,915

[22] Filed: Nov. 23, 1981

[51] Int. Cl.³ .............................................. A61F 13/16
[52] U.S. Cl. ..................................................... 604/396
[58] Field of Search ............... 604/387, 393, 394, 396, 604/397, 402; 2/409

[56] References Cited

U.S. PATENT DOCUMENTS

| Re. 25,360 | 3/1963 | Rice | 2/409 |
| 2,102,359 | 12/1937 | Frieman | 604/396 |
| 2,494,292 | 1/1950 | Frazer | 604/396 |
| 3,287,739 | 11/1966 | Kaplan | 2/409 |
| 3,678,515 | 7/1972 | Wehrmann | 2/409 |

Primary Examiner—C. Fred Rosenbaum
Attorney, Agent, or Firm—Bauer & Amer

[57] ABSTRACT

A pantyhose garment having in the panty portion thereof a fluid-tight compartment for conveniently supporting an absorbent material therein as a sanitary napkin, whereby the napkin in its operative position is exposed through an opening to receive fluids discharged from the body of the user to which the garment is applied and effectively restrained from relative movement so as to maintain its said operative position.

1 Claim, 4 Drawing Figures

PANTYHOSE WITH SANITARY NAPKIN HOLDER

The present invention relates to an improved sanitary napkin holder, and more particularly to improved means for the effective sealed confinement of the napkin during an interval of use, as well as for effectively maintaining the operative position thereof.

It is already well known, according to the sanitary napkin holder of U.S. Pat. No. 3,079,922, that ease and comfort during the use of a sanitary napkin can be effectively promoted by suspending the holder from an appropriate belt or harness. This type support, however, detracts from fluidtight confinement of the napkin, which is an equally important requirement.

Broadly, it is an object of the present invention to provide an effectively sealed sanitary napkin holder overcoming the foregoing and other shortcomings of the prior art. Specifically, it is an object to embody the holder in a pantyhouse so as to utilize the elastic thereof, particularly about the leg openings, to contribute to the sealing of the napkin as well as to maintaining an effective operative position thereof, which position also contributes to comfort during the wearing of the pantyhose. That is, the within pantyhose with its integrally embodied sanitary napkin holder does not twist or otherwise lose its proper position for fit during wearing service by the user.

A pantyhose with a built-in sanitary napkin holder demonstrating objects and advantages of the present invention is one having a front, rear and opposite sides cooperating to define a lower torso garment having an upper elasticized waist opening and right and left elasticized leg openings. A sanitary napkin compartment is formed of two fluid-tight plies disposed in facing, superposed relation to each other in the crotch area of the panty portion of the pantyhose. The compartment is oriented to extend between the front and rear of the panty and in spanning relation between the elasticized leg openings, such that length portions of the elastomeric content of the leg openings form the opposite side edges of the compartment. In this manner, gripping contact of the elasticized portions is established with the user's legs to contribute to an optimum sealed confinement of the sanitary napkin in said compartment during wearing service of the pantyhose, and there is also effectively promoted a comfortable and properly-positioned fit of the pantyhose on the user.

The above brief description, as well as further objects, features and advantage of the present invention, will be more fully appreciated by reference to the following detailed description of a presently preferred, but nonetheless illustrative embodiment in accordance with the present invention, when taken in conjunction with the accompanying drawings, wherein.

Figure 1:
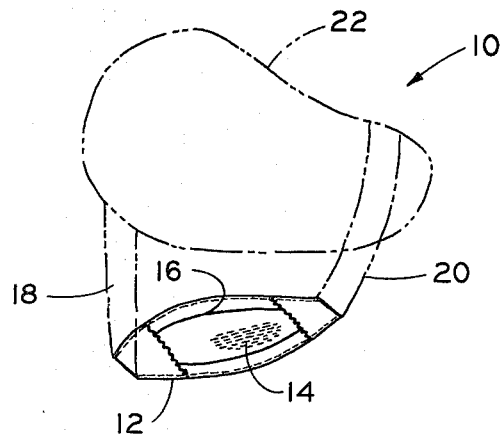
FIG. 1 is a perspective view of a prior art sanitary napkin holder.
Figure 2:
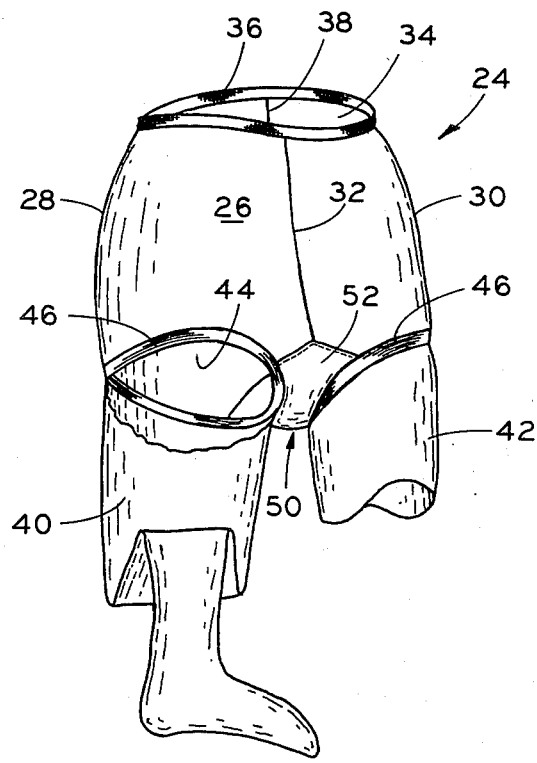
FIG. 2 is a perspective view of a pantyhose with a sanitary napkin holder in accordance with the present invention, wherein portions thereof are broken away to better illustrate structural features thereof.

The within pantyhose embodies the inventive concept of the "Panty With Sanitary Napkin Holder" described and illustrated in U.S. Pat. No. 4,044,769 which is incorporated herein in its entirety. As explained in the referred patent, and as is illustrated in FIG. 1 hereof, a typical prior art garment 10 with an associated sanitary napkin holder includes the holder per se, designated 12, in which there is placed an absorbent material serving as a so-called sanitary napkin 14 which is exposed for the purposes intended through an opening 16 in the holder 12. As further illustrated in FIG. 1, the holder 12 is typically supported in the crotch area by front and rear straps 18 and 20 from an elasticized waist encircling band 22. Among other shortcomings, the prior art garment 10 shifts in position relative to the wearer since it is not an integral part of a more basic garment that effectively retains its wearing position on the user. Overcoming the just noted shortcoming, and providing other advantages as well, is the panty garment with an integral sanitary napkin holder as described and illustrated in the referred to U.S. Pat. No. 4,044,769. The inventive concept of the referred to patent is herein described and illustrated as embodied in a pantyhose, which, as is well understood, is a basic garment related to a panty per se. More particularly, and as illustrated in FIG. 2, a typical pantyhose, generally designated 24 includes a panty 26 per se which has a front and rear provided by opposite sides 28 and 30 which are connected to each other along front and rear seams 32 and 34.

Horizontally oriented elastomeric yarns, individually and collectively designated 36, are provided at the upper portion of the panty portion 26 to thereby bound a waist opening 38. As the name "pantyhose" implies, connected to the panty portion 26 are a pair of left and right stockings 40 and 42, the upper portion of each of which is connected to what constitutes the leg openings 44 for the right and left legs of the user. In a typical pantyhose, each of the leg openings 44 is bounded by elastomeric yarns, individually and collectively designated 46, which are essentially horizontally oriented at the juncture of the stockings 40 and 42 with the panty portion 26. The elastomeric yarns 46 serve the important function of maintaining the area in which they are embodied firmly against the legs of the user. Such yarns, together with the yarns 36 which define the waist opening 38 in the upper portion of the panty 26, maintain the position of the panty 26, as well as the attached stockings 40 and 42 which extend therefrom that feels comfortable to the user during bodily movements of the user.

In accordance with the present invention, there is embodied as an integral part of the pantyhose 24, and more particularly in the panty portion 26 thereof, a sanitary napkin holder, generally designated 50. Said sanitary napkin holder, as is perhaps best illustrated in FIG. 2, is located in the crotch area 52 of the panty portion 26 of the pantyhose garment 24.

Figure 3:
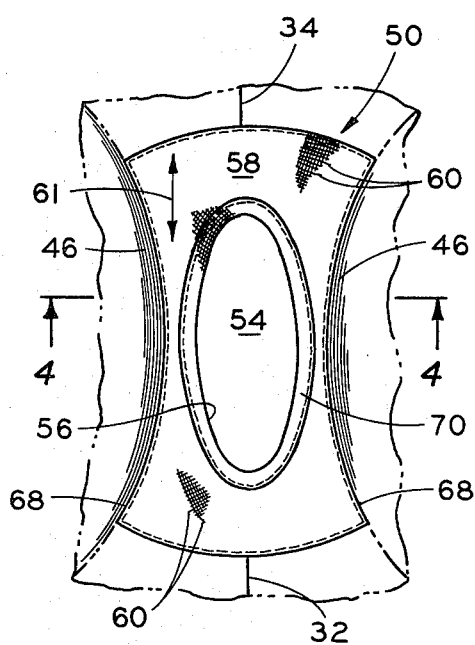
FIG. 3 is a partial front elevational view, on an enlarged scale, of the sanitary napkin holder.

Referring now more particularly to FIG. 3, it will be noted that the holder 50 extends both lengthwise and widthwise of the crotch area 52. In the widthwise dimension, said holder 50 extends between the panty portion embodying the elastomeric yarns 46 for both the left and right legs. The absorbent material functions as a sanitary napkin 54 and in its operative position is properly exposed through an oval-shaped opening 56. It should be understood that the upper ply 58 of the construction which provides the holder 50 has elastomeric yarns, individually and collectively designated 60, which are oriented lengthwise of the ply 58. The significance of this is that the urgency of the elastomeric content that is exerted by the yarns 60 is essentially in the direction of the double-headed arrow 61, rather than in a direction tranverse thereto. Because the urgency of the elastomeric content of the ply 58 is not exerted transverse to the direction 61, there is no tendency or force urgency to pull the leg opening portions 46 of the stockings 40, 42 away from their established contact with the user's legs. This, in turn, contributes to maintaining proper fit of the garment on the user, and also enables the elastomeric yarns 46 to effectuate a seal against any inadvertent leakage of fluid that does not come into absorbing contact with the napkin 53.

Figure 4:
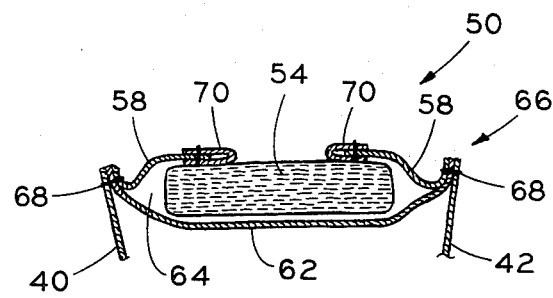
FIG. 4 is a side elevational view, in section, taken along line 4—4 of FIG. 3, illustrating further structural details.

For completness sake and also to fully understand the construction of the pantyhose sanitary napkin holder 50 hereof, reference should be made to FIG. 4 in which it is best illustrated that ply 58 cooperates with an underply 62 to form a compartment 64 sized to receive therein a compressed and shaped wad of absorbent material 54. To embody the holder 50 as an integral part of the panty portion 26 of the garment 24, the plies 58 and 62 are bar-tacked at their peripheral edges, as at 66, and are then joined by a seam 68 along the portion of the stockings 40 and 42 which are adjacent to the crotch area 52 of the pantyhose garment 24. To provide a finished edge around the oval opening 56, the edge of ply 58 which bounds this opening has attached thereabout a piping 70.

In a preferred commercial embodiment ply 58 will be understood to be die cut from, or otherwise fabricated from, any one of several commercially available stretch fabrics. Also, this ply is advantageously comprised as a lamination with a thin gauge plastic, so as to be rendered fluid-tight. The underply 62 is also preferably a lamination which is fluid-tight.

From the foregoing, it should be readily appreciated that there has been described herein a sanitary napkin holder 50 effectively embodied in the construction of a pantyhose 24 in such a way as to leave intact the ability of the panty portion 26 thereof to maintain its position relative to the user, and thus to correspondingly provide this advantage also for the napkin 54 in its operative position in the holder. In addition, the within holder effectively utilizes the elasticized yarn content of the garment to contribute to providing an effective fluid-tight confinement of the sanitary napkin.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

What is claimed is:

1. In combination, a pantyhose comprised of a panty having a front, rear and opposite sides cooperating to define a lower torso garment having a waist opening and edges bounding right and left leg openings and of left and right leg-receiving stockings respectively attached as extensions from said right and left leg openings, elastomeric yarns secured along said waist and leg openings to urge edges bounding the latter into gripping contact with the user's legs to contribute to an optimum sealed confinement for a sanitary napkin during wearing service of such pantyhose, and a sanitary napkin compartment formed of plies of fluid-tight material disposed in facing, superposed relation to each other in the crotch area of said pantyhose, the upper ply of said compartment being oriented to extend between the front and rear of said portion of said pantyhose and in substantial spanning relation between said elastomeric yarns bounding said leg openings, said compartment upper ply being further adapted to receive thereunder as a sanitary napkin a fluid absorbent material that is exposed to the interior of said panty portion of said pantyhose and having an oblong edge bounding an opening therein extending for a substantial portion of the length of said compartment and for a width of said compartment sufficient to receive fluids discharged from the body of the user without side leakage from said compartment, said compartment upper ply being constructed of elastomeric yarns oriented substantially parallel to the elastomeric yarns of said leg openings and having a non-stretchable strip secured about said oblong edge thereof so as to retain the sides of said compartment upper ply about the absorbent material in said compartment without adverse effect on said seal of said elastized leg openings, said panty portion of said pantyhose supporting said compartment in position on the user such that the opening is restrained from movement relative to the body so that the compartment opening will remain in position to enable the absorbent material to receive the discharged body fluids.

* * * * *